(12) United States Patent
Masuda et al.

(10) Patent No.: US 8,716,031 B2
(45) Date of Patent: May 6, 2014

(54) METHOD FOR QUANTIFICATION OF ANTIGEN-SPECIFIC CANINE IGE

(75) Inventors: Kenichi Masuda, Kanagawa (JP); Yasuyuki Ishii, Kanagawa (JP); Nobutaka Yasuda, Kanagawa (JP)

(73) Assignees: RIKEN, Wako (JP); Animal Allergy Clinical Laboratories, Sagamihara (JP)

( * ) Notice: Subject to any disclaimer, the term of this patent is extended or adjusted under 35 U.S.C. 154(b) by 495 days.

(21) Appl. No.: 12/992,476

(22) PCT Filed: May 12, 2009

(86) PCT No.: PCT/JP2009/058831
§ 371 (c)(1),
(2), (4) Date: Jan. 12, 2011

(87) PCT Pub. No.: WO2009/139378
PCT Pub. Date: Nov. 19, 2009

(65) Prior Publication Data
US 2011/0111529 A1    May 12, 2011

(30) Foreign Application Priority Data

May 12, 2008    (JP) ................. 2008-125292

(51) Int. Cl.
| | | |
|---|---|---|
| *C07K 16/06* | (2006.01) |
| *C07K 16/42* | (2006.01) |
| *G01N 33/53* | (2006.01) |
| *G01N 33/536* | (2006.01) |
| *G01N 33/537* | (2006.01) |
| *G01N 33/543* | (2006.01) |
| *G01N 33/563* | (2006.01) |
| *G01N 33/96* | (2006.01) |
| *G01N 33/68* | (2006.01) |
| *C12N 5/20* | (2006.01) |
| *C12N 5/16* | (2006.01) |

(52) U.S. Cl.
CPC ............ *G01N 33/6854* (2013.01); *G01N 33/96* (2013.01); *G01N 33/536* (2013.01); *G01N 33/537* (2013.01); *G01N 33/543* (2013.01); *G01N 2333/435* (2013.01); *G01N 2469/20* (2013.01); *G01N 2496/05* (2013.01); *G01N 2800/24* (2013.01); *C07K 16/06* (2013.01); *C07K 16/42* (2013.01); *C07K 16/4291* (2013.01); *C12N 5/163* (2013.01); *Y10S 435/975* (2013.01)
USPC ............ 436/513; 435/7.1; 435/7.5; 435/7.92; 435/7.94; 435/7.95; 435/70.21; 435/337; 435/975; 436/518; 436/536; 436/8; 436/16; 530/388.1; 530/388.25; 530/389.1; 530/391.1; 530/391.3

(58) Field of Classification Search
CPC .... C07K 16/06; C07K 16/42; C07K 16/4291; C12N 5/163; G01N 33/53; G01N 33/536; G01N 33/537; G01N 33/543; G01N 33/6854; G01N 33/96; G01N 2033/53; G01N 2333/435; G01N 2469/20; G01N 2496/05; G01N 2800/24
USPC ........ 435/7.1, 7.21, 7.5, 7.8, 7.92, 7.94, 7.95, 435/69.3, 975, 70.21, 337; 436/501, 513, 436/518, 536, 547, 8, 16; 530/388.1, 389.1, 530/391.1, 391.3, 388.25
See application file for complete search history.

(56) References Cited

U.S. PATENT DOCUMENTS

| | | | |
|---|---|---|---|
| 4,201,221 | A | 5/1980 | Ali et al. |
| 4,845,027 | A | 7/1989 | Calenoff et al. |
| 4,849,337 | A | 7/1989 | Calenoff et al. |
| 5,945,294 | A * | 8/1999 | Frank et al. ............. 435/7.9 |
| 7,148,023 | B2 * | 12/2006 | Hammerberg ............. 435/7.1 |
| 7,279,295 | B2 | 10/2007 | Dewitt et al. |
| 7,470,773 | B2 | 12/2008 | Hammerberg |
| 2003/0109067 | A1 | 6/2003 | Brown et al. |
| 2004/0014155 | A1 | 1/2004 | Dewitt et al. |
| 2007/0190668 | A1 | 8/2007 | Brown et al. |

Standard curve generated with sensitized mouse serum

FOREIGN PATENT DOCUMENTS

| | | |
|---|---|---|
| JP | 8-511621 T | 12/1996 |
| JP | 11-142403 A | 5/1999 |
| JP | 2000-266748 A | 9/2000 |
| JP | 2000-321274 A | 11/2000 |
| JP | 2001-074737 A | 3/2001 |
| JP | 2002-514306 A | 5/2002 |
| JP | 2005-538040 A | 12/2005 |
| JP | 2006-151880 A | 6/2006 |
| WO | WO 94/29696 A1 | 12/1994 |
| WO | WO 98/53321 A1 | 11/1998 |

OTHER PUBLICATIONS

Hamada et al., 2003. Allergen-independent maternal transmission of asthma susceptibility. Journal of Immunology 170: 1683-1689.*
Gebhard et al., *Immunology*, 85: 429-434 (1995).
Kawahara et al., *Journal of Immunological Methods*, 233: 33-40 (2000).
Leimgruber et al., *Clinical and Experimental Allergy*, 21: 127-131 (1991).
Sakaguchi et al., *Veterinary Immunology and Immunopathology*, 83: 69-77 (2001).
Stedman et al., *Veterinary Immunology and Immunopathology*, 78: 349-355 (2001).
Okayama et al., *Veterinary Immunology & Immunopathology*, 139: 99-106 (2011).
European Patent Office; Extended European Search Report in European Patent Application No. 09746584.3 (Sep. 13, 2011).

* cited by examiner

*Primary Examiner* — Mark Shibuya
*Assistant Examiner* — James L Grun
(74) *Attorney, Agent, or Firm* — Leydig, Voit & Mayer, Ltd.

(57) ABSTRACT

Disclosed is a convenient and effective means for quantifying an antigen-specific canine or human IgE. Specifically disclosed is a method for quantifying an antigen-specific canine IgE, which comprises the following steps (A) to (D): (A) contacting a biological sample collected from a subject with an antigen to conjugate IgE contained in the sample with the antigen; (B) measuring the quantity of IgE in a standard sample collected from an experimental animal which is different from the subject and has been sensitized with the same antigen as that used in step (A) by using a substance capable of recognizing both IgE from the subject and IgE from the experimental animal, thereby producing a standard curve; (C) detecting a conjugate formed in step (A) by using the same substance capable of recognizing both IgE from the subject and IgE from the experimental animal as that used in step (B); and (D) determining the quantity of IgE in the biological sample collected from the subject by utilizing the quantity of the conjugate detected in step (C) and the standard curve produced in step (B). Also specifically disclosed is a method for quantifying an antigen-specific human IgE.

7 Claims, 4 Drawing Sheets

METHOD FOR QUANTIFICATION OF ANTIGEN-SPECIFIC CANINE IGE

TECHNICAL FIELD

The present invention relates to a method of quantitatively measuring antigen-specific immunoglobulin E (IgE) in dogs or humans, specifically to the fields of allergy tests and allergy diagnoses for dogs or humans.

BACKGROUND ART

Allergy tests for dogs are usually based on qualitative determination of positivity or negativity for antigens or relative determination of IgE whose levels are expressed by a laboratory unit defined by the clinical laboratory, with no quantitative determination performed for antigen-specific IgE, which can serve as an absolute index of allergies. This is also true for allergy tests for humans. Known conventional arts for measuring IgE include antigen-specific 1-stage assay (Patent Document 1), a strip test for in vitro allergy diagnosis (Patent Document 2), an immunological test for dietary allergic substances (Patent Document 3), clinical utility of qualitative determination of IgE in humans (Non-patent Document 1), a method of relative quantitation of canine IgE whose levels are expressed by a laboratory unit (Non-patent Document 2), a method of producing a human IgE-producing hybridoma (Non-patent Document 3), an antigen-specific canine IgE monoclonal antibody and preparation method thereof (Patent Document 4, Non-patent Document 4), the high-affinity IgE receptor α subunit (FcεRIα) (Non-patent Document 5) and the like. Although these conventional arts have realized qualitative or relatively quantitative determination of IgE, no method of absolute quantitation of antigen-specific IgE has been realized. Quantitation of antigen-specific IgE cannot be realized unless the following problems are solved.

(1) Problems with the Unit of Indication

A quantitative test of an antigen-specific IgE has been established in laboratory-based settings for some antigens (Japanese cedar pollen antigen and the like), wherein a standard curve is generated using a serum of a dog shown by an intradermal reaction to have been sensitized to an antigen X as "a standard serum" on the presumption that the serum contains specific IgE against the antigen X (Non-patent Document 2). In this method, however, because the standard serum used is set at each laboratory, antigen-specific IgE assay values are indicated by Laboratory Unit/ml. Therefore, the unit of indication is distinctly set for each experiment at each laboratory; if different experimental systems or different laboratories are involved, it is unavoidable to use different standard sera even for the same assay system, so that measured values could not be compared as they were. Even for an antigen-specific IgE assay system within the same laboratory, any different antigen necessitates the use of serum sensitized with the antigen, so that it has been impossible to unify the unit of indication for the different antigens. Therefore, even using the same assay system, a comparison of the amount of antigen-specific IgE between different antigens has been impossible (even when the same Laboratory Unit/ml is used, a comparison between different antigens is impossible). These circumstances are nearly the same as those in humans (Non-patent Document 1).

(2) Problems with Purification of Antigen-Specific IgE

A method of purifying desired antigen-specific canine IgE from a serum of a sensitized dog is theoretically possible. Because the dog essentially has a large amount of total IgE, a purification step in two stages is required for this purpose. First, total IgE in the serum is purified using an IgE adsorption column, and then an antigen-specific IgE is purified using an object antigen-adsorbing column. However, although this method enables purification of total IgE, purification of the antigen-specific IgE poses a major problem concerning whether or not the antigen-specific IgE adsorbed to the column can be successfully eluted and extracted because IgE strongly binds to antigens. For this reason, there have been no reported cases where antigen-specific IgE was actually purified by the above-described method using a canine or human serum, though there has been a case of purification of total IgE (Patent Document 4).

(3) Problems with Preparation of Hybridomas that Produce Antigen-Specific Canine IgE If an antigen-specific canine IgE-producing hybridoma cell line can be established, it will be no longer necessary to purify antigen-specific canine IgE from a serum. To this end, in case of dogs, it is indispensable to prepare an antigen-sensitized dog and fuse cells of lymph nodes or spleen thereof, or peripheral blood lymphocytes cultured with stimulation with the object antigen, with mouse myeloma cells. However, the probability of successful fusion by this method is extremely low; only one clone (canine IgE against nematodal antigen) has been prepared to date (Non-patent Document 4). Moreover, even if the cell fusion is successful, a period of 1 year or more is taken to sort the desired clone and establish it as a cell line, so that this approach is impractical when several tens of kinds of antigens are involved. In human cases, it is ethically difficult to prepare such a hybridoma.

(4) Problems with Preparation Cost

If the standard serum to be used in (1) is prepared using an experimental dog, much cost is taken, posing a major problem. For example, with the assumption of a rearing cost of 30000 yen/dog/month as calculated from a purchasing cost of 100000 to 200000 yen per dog and duration of preparation of sensitized serum of 2 months, preparation of the standard serum will take at least 160000 to 260000 yen per antigen. Therefore, establishing an antigen-specific IgE quantitative testing system for 50 antigens will cost 8000000 to 13000000 yen. Although sensitizing one dog with several kinds of antigens may be considered to reduce the cost, the problem of unwanted detection of the cross-reactivity among the different antigens cannot be solved. Additionally, although a large amount of 100 to 200 mL of serum can be collected from one sensitized dog at one time (equivalent to daily measurements for 300 years), such a large amount is unnecessary for performing the examination. Rather, considering the freezer space for long-term storage of the serum and the like, the cost performance of preparing a sensitized dog is much worse than a mouse. In human cases, it is ethically impossible to prepare a standard serum.

PRIOR ART REFERENCES

Patent Documents patent document 1: National Publication of International Patent Application No. 8-511621
patent document 2: National Publication of International Patent Application No. 2002-514306
patent document 3: JP-A-H11-142403
patent document 4: JP-A-2006-151880

Non-Patent Document non-patent document 1: Clin Exp Allergy 21, 127-31 (1991)
non-patent document 2: Vet Immunol Immunopathol. 83, 69-77 (2001)
non-patent document 3: J. Immunol. Methods 233, 33-40 (2000)
non-patent document 4: Immunology 85, 429-34 (1995)

non-patent document 5: Vet Immunol Immunopathol. 78, 349-55 (2001)

SUMMARY OF THE INVENTION

Problems to be Solved by the Invention

A problem to be solved by the present invention is to provide a convenient and effective means of quantitation of antigen-specific canine and human IgEs.

Means of Solving the Problems

The present inventors extensively investigated to solve the above-described problem, and as a result discovered an antibody that also recognizes canine IgE among rat monoclonal antibodies that recognize mouse IgE, demonstrated that antigen-specific canine IgE can be quantified by generating a standard curve with sera from an antigen-sensitized mouse whose total amount of antigen-specific IgE is determined, using this antibody, further showed that antigen-specific human IgE can also be quantified in the same way, and have completed the present invention.

Accordingly, the present invention is as follows:

[1] A method of quantifying an antigen-specific canine IgE, comprising the following steps (A) to (D):
(A) a step for contacting a biological sample from a subject dog with an antigen to bind the IgE in the sample and the antigen,
(B) a step for measuring the IgE in a standard sample of a laboratory animal other than dog, sensitized with the antigen of the step (A), using a substance that recognizes canine IgE and also recognizes the IgE of the laboratory animal, and generating a standard curve,
(C) a step for detecting the conjugate formed in the step (A) using the substance that recognizes canine IgE and also recognizes the IgE of a laboratory animal other than dog, used in the step (B), and
(D) a step for quantifying the amount of IgE in the biological sample from the subject dog using the amount of conjugate detected in the step (C) and the standard curve generated in the step (B).

[2] A method of diagnosing an allergic disease, comprising the following steps (A) to (E):
(A) a step for contacting a biological sample from a subject dog with an antigen to bind the IgE in the sample and the antigen,
(B) a step for measuring the IgE in a standard sample of a laboratory animal other than dog, sensitized with the antigen of the step (A), using a substance that recognizes canine IgE and also recognizes the IgE of the laboratory animal, and generating a standard curve,
(C) a step for detecting the conjugate formed in the step (A) using the substance that recognizes canine IgE and also recognizes the IgE of the laboratory animal other than dog, used in the step (B),
(D) a step for quantifying the amount of IgE in the biological sample from the subject dog using the amount of conjugate detected in the step (C) and the standard curve generated in the step (B), and
(E) a step for determining the presence or absence or severity of an allergic disease on the basis of the results of the quantitation in the step (D).

[3] The method described in [1] or [2], wherein the steps (A), (B), (C) and (D) are performed for each antigen concurrently or separately.

[4] The method described in [1] or [2], wherein the step (B) is performed concurrently with, or separately from, the steps (A), (C) and (D).

[5] The method described in any one of [2] to [4], wherein the allergic disease is at least 1 kind selected from the group consisting of pollenosis, allergic rhinitis, allergic conjunctivitis, bronchial asthma, atopic dermatitis, contact dermatitis, post-vaccination allergy, anaphylaxis, food allergy, a disease causing hyper-IgE-emia, and a disease estimated to involve IgE in the pathology thereof.

[6] The method described in any one of [1] to [5], wherein the biological sample from the subject dog is blood, serum, blood plasma, nasal discharge, tear, saliva, urine or feces.

[7] The method described in any one of [1] to [6], wherein the antigen is at least 1 kind selected from the group consisting of plant pollen, dried leave/stem or latex, food extract, fungal extract and arthropod body extract.

[8] The method described in any one of [1] to [6], wherein the antigen is at least 1 kind selected from the group consisting of pollen, dried leave/stem or latex of alder, rubber tree, Bermuda grass, Japanese white birch, English daisy, dandelion, goldenrod, orchard grass, ragweed, sweet vernal grass, timothy, Japanese cedar and Japanese cypress; food extract from wheat, turkey, soybean, salmon, rye, rice, potato, pork, cow's milk, mutton, egg yolk, egg white, corn, fruit, cod, chicken, catfish, beef, night smelt, crab, shrimp and ascidian; fungal extract from the genus *Alternaria*, the genus *Penicillium* and *Cladosporium*; and bug body extract from mite/tick, flea, mosquito, cockroach and moth.

[9] The method described in any one of [1] to [8], wherein the substance is an antibody that recognizes both canine IgE and the IgE of a laboratory animal other than dog.

[10] The method described in any one of [1] to [9], wherein the laboratory animal is an animal selected from the group consisting of mouse, rat, guinea pig, hamster and rabbit.

[11] A quantitation kit for antigen-specific canine IgE comprising a substance that recognizes canine IgE and also recognizes the IgE of a laboratory animal other than dog, an antigen, and a standard sample from the laboratory animal sensitized with the antigen, contained in separate containers.

[12] A diagnostic kit for a canine allergic disease comprising a substance that recognizes canine IgE and also recognizes the IgE of a laboratory animal other than dog, an antigen, a standard sample from the laboratory animal sensitized with the antigen, and a control sample from the laboratory animal not suffering any allergic disease, contained in separate containers.

[13] The kit described in [12], wherein the allergic disease is at least 1 kind selected from the group consisting of pollenosis, allergic rhinitis, allergic conjunctivitis, bronchial asthma, atopic dermatitis, contact dermatitis, post-vaccination allergy, anaphylaxis, food allergy, a disease causing hyper-IgE-emia and a disease estimated to involve IgE in the pathology thereof.

[14] The kit described in any one of [11] to [13], wherein the antigen is at least 1 kind selected from the group consisting of plant pollen, dried leave/stem or latex, food extract, fungal extract and arthropod body extract.

[15] The kit described in any one of [11] to [14], wherein the substance is an antibody that recognizes both canine IgE and the IgE of a laboratory animal other than dog.

[16] The kit described in any one of [11] to [15], wherein the laboratory animal is an animal selected from the group consisting of mouse, rat, guinea pig, hamster and rabbit.

[17] A method of quantifying antigen-specific human IgE, comprising the following steps (A) to (D):
(A) a step for contacting a biological sample from a human subject with an antigen to bind the IgE in the sample and the antigen,
(B) a step for measuring the IgE in a standard sample from a laboratory animal sensitized with the antigen of the step (A), using a substance that recognizes human IgE and also recognizes the IgE of the laboratory animal, and generating a standard curve,
(C) a step for detecting the conjugate formed in the step (A), using the substance that recognizes human IgE and also recognizes the IgE of the laboratory animal, used in the step (B), and
(D) a step for quantifying the amount of IgE in the biological sample from the human subject using the amount of conjugate detected in the step (C) and the standard curve generated in the step (B).
[18] The method described in [17], wherein the steps (A), (B), (C) and (D) are performed for each antigen concurrently or separately.
[19] The method described in [17], wherein the step (B) is performed concurrently with, or separately from, the steps (A), (C) and (D).
[20] The method described in any one of [17] to [19], wherein the biological sample from the human subject is blood, serum, blood plasma, nasal discharge, tear, saliva, urine or feces.
[21] The method described in any one of [17] to [20], wherein the antigen is at least 1 kind selected from the group consisting of plant pollen, dried leave/stem or latex, food extract, fungal extract and arthropod body extract.
[22] The method described in any one of [17] to [20], wherein the antigen is at least 1 kind selected from the group consisting of pollen, dried leave/stem or latex of alder, rubber tree, Bermuda grass, Japanese white birch, English daisy, dandelion, goldenrod, orchard grass, ragweed, sweet vernal grass, timothy, Japanese cedar and Japanese cypress; food extract from wheat, turkey, soybean, salmon, rye, rice, potato, pork, cow's milk, mutton, egg yolk, egg white, corn, fruit, cod, chicken, catfish, beef, night smelt, crab, shrimp and ascidian; fungal extract from the genus *Alternaria*, the genus *Penicillium* and *Cladosporium*; and bug body extract from mite/tick, flea, mosquito, cockroach and moth.
[23] The method described in any one of [17] to [22], wherein the substance is an antibody that recognizes both human IgE and the IgE of the laboratory animal.
[24] The method described in any one of [17] to [23], wherein the laboratory animal is an animal selected from the group consisting of mouse, rat, guinea pig, hamster, rabbit, dog, sheep, goat, pig and monkey.
[25] A quantitation kit for antigen-specific human IgE comprising a substance that recognizes human IgE and also recognizes the IgE of a laboratory animal, an antigen, and a standard sample from the laboratory animal sensitized with the antigen, contained in separate containers.
[26] A diagnostic reagent for a human allergic disease comprising a substance that recognizes human IgE and also recognizes the IgE of a laboratory animal.
[27] A diagnostic kit for a human allergic disease comprising a substance that recognizes human IgE and also recognizes the IgE of a laboratory animal, an antigen, a standard sample from the laboratory animal sensitized with the antigen, and a control sample from the laboratory animal not suffering any allergic disease, contained in separate containers.
[28] The diagnostic reagent described in [26] or the kit described in [27], wherein the allergic disease is at least 1 kind selected from the group consisting of pollenosis, allergic rhinitis, allergic conjunctivitis, bronchial asthma, atopic dermatitis, contact dermatitis, post-vaccination allergy, anaphylaxis, food allergy, a disease causing hyper-IgE-emia and a disease estimated to involve IgE in the pathology thereof.
[29] The kit described in [25] or [27], wherein the antigen is at least 1 kind selected from the group consisting of plant pollen, dried leave/stem or latex, food extract, fungal extract and arthropod body extract.
[30] The kit described in [25] or [27] or the diagnostic reagent described in [26], wherein the substance is an antibody that recognizes both human IgE and the IgE of a laboratory animal.
[31] The kit described in [25] or [27] or the diagnostic reagent described in [26], wherein the laboratory animal is an animal selected from the group consisting of mouse, rat, guinea pig, hamster, rabbit, dog, sheep, goat, pig and monkey.

Effect of the Invention

According to the method of quantification of the present invention, the amount of antigen-specific canine or human IgE can be known accurately, making it possible to trace the seasonality of allergies and monitor therapeutic effects in the fields of veterinary medicine and clinical medicine. The method of quantification, diagnostic method or diagnostic reagent of the present invention makes it possible to compare the amount of the antigen-specific IgE between different antigens, thus enabling a determination of which antigen is currently problematic in each dog or human suffering an allergic disease. According to the kit of the present invention, the method of quantification and diagnostic method of the present invention can be carried out conveniently and quickly.

MODE FOR CARRYING OUT THE INVENTION

Figure 1:
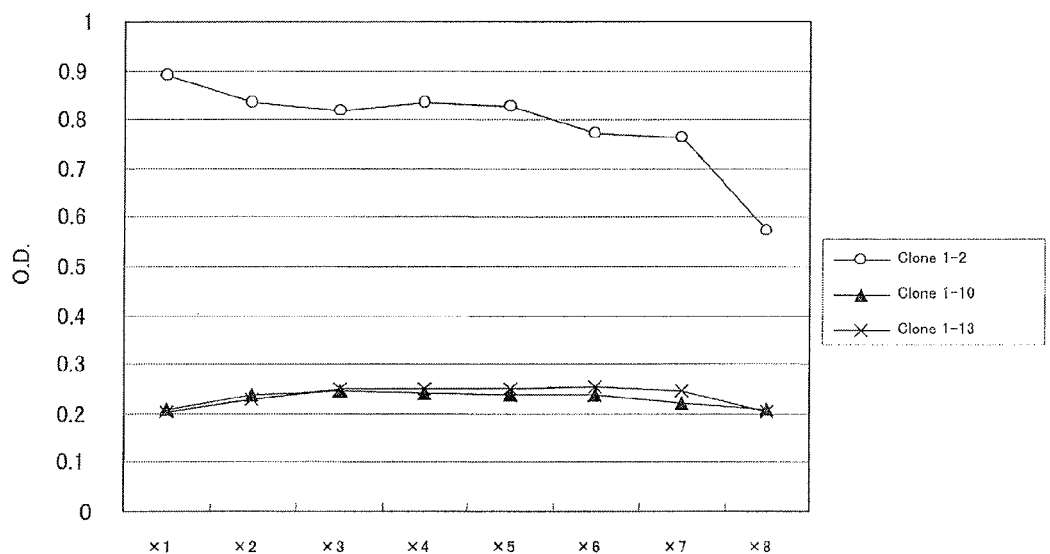
FIG. 1 A graph showing that rat anti-canine IgE antibodies (clones) recognize mouse IgE in an examination using the ELISA method. The axis of ordinates and the axis of abscissa indicate absorbance and dilution rate of antibody preparation, respectively.

In the present invention, "an antigen" refers to a substance possessing immunogenicity against at least dogs or humans, preferably referring to a substance possessing immunogenicity against both the dog and a laboratory animal other than dog, or against both the human being and a laboratory animal. The antigen is often a protein or a glycoprotein, but is not limited thereto. Examples of the antigen include pollen, dried leave/stem or latex of alder, rubber tree, Bermuda grass, Japanese white birch, English daisy, dandelion, goldenrod, orchard grass, ragweed, sweet vernal grass, timothy, Japanese cedar and Japanese cypress; food extract from wheat, turkey, soybean, salmon, rye, rice, potato, pork, cow's milk, mutton, egg yolk, egg white, corn, fruit, cod, chicken, catfish, beef, night smelt, crab, shrimp and ascidian; fungal extract from the genus *Alternaria*, the genus *Penicillium* and *Cladosporium*; and bug body extract from mite/tick, flea, mosquito, cockroach and moth, and the like. Although these are antigens currently known as causal substances that cause allergies, antigens that will be found as causal substances for allergies in the future can also be used in the present invention.

The aforementioned antigen may be used as a commercial product as it is, or after being extracted and purified from a plant- or animal-derived substance by a conventional method.

In the present invention, "IgE" is a kind of immunoglobulin which is a protein molecule produced by B cells by the action of helper T cells and the like that have received signals of various antigens invading a living organism, and having the capability of binding to IgE receptors on the cell surfaces of mast cells and basophils. IgE is a protein molecule having the property of binding specifically to the various antigens to thereby provoke degranulation of mast cells, basophils and the like and cause histamine release and the like.

In the present invention, "a biological sample" is not particularly limited, as far as it is a component or tissue derived from a living organism, isolatable from the living organism, and possibly containing IgE; such samples include parts of tissues of living organisms (bronchial mucosa, nasal mucosa, gastric mucosa, intestinal mucosa, oral mucosa and the like), body fluids (blood, serum, blood plasma, nasal discharge, tear, saliva, urine, feces, sputum, gastric juice and the like) and the like. The biological sample used may be collected from a subject dog or a human subject according to a conventional method, used as it is or after being pre-treated according to a conventional method as desired.

In the present invention, a "sensitized" laboratory animal refers to an animal that has been brought into contact with a particular antigen to come to produce an IgE that recognizes the antigen. Modes of contact with the antigen include aspiration, oral ingestion, injection in the body (subcutaneous administration and the like) and the like. In the sensitized laboratory animal, there are some cases where the amount of antigen-specific IgE and the amount of total IgE in the blood can be regarded as having become equal as a result of contact with the antigen, and other cases where the amount of antigen-specific IgE is lower than the amount of total IgE. In the present invention, by measuring the amount of antigen-specific IgE and the amount of total IgE in a previously "sensitized" laboratory animal, a biological sample from any laboratory animal can be used as a standard sample.

In the present invention, "a laboratory animal" refers to an animal supplied for experimental purposes wherein the animal is other than the dog which is the subject of measurement, in case of quantitation of canine IgE. The laboratory animal is preferably a small animal with clear genetic background being reared under SPF conditions; specifically, such animals include rodents such as mice, rats, guinea pigs, hamsters, and rabbits. The laboratory animal is more preferably one for which a means for separately measuring the amount of total IgE in its biological sample is already available. In case of quantitation of human IgE, "a laboratory animal" is not particularly limited, as far as it is a non-human animal capable of producing IgE; such animals include mice, rats, guinea pigs, hamsters, rabbits, dogs, sheep, goat, pigs, monkeys and the like. Of animals other than humans, small animals with clear genetic background being reared under SPF conditions are preferred, with greater preference given to ones for which a means for separately measuring the amount of total IgE in the biological sample is already available.

In the present invention, "a standard sample from a laboratory animal" refers to a biological sample from a sensitized laboratory animal, for generating a standard curve in the method of the present invention. The standard sample is preferably blood, serum, or blood plasma, which are in common use for measuring IgE. A monoclonal IgE against a certain antigen (for example, mouse anti-ovalbumin IgE and the like), if any, can be used as a standard sample.

In the present invention, "a standard curve" refers to a curve determined by an approximation expression to know the concentration of an antigen-specific IgE according to the assay method for the IgE. The standard curve is drawn by plotting measured values and tying them on a curve for the positional relationship of the plots, with the concentration of the aforementioned standard sample in serial dilutions indicated by the axis of abscissa (the axis of ordinates), and the amount of antigen-bound IgE in the standard sample indicated in an arbitrary unit by the axis of ordinates (the axis of abscissa). The standard curve can be shown approximately as a straight line by logarithmically expressing the obtained values on the two axes. In the present invention, the standard curve is generated for each antigen as a rule, but a common standard curve may be generated for different antigens with crossreactivity and used to determine the concentrations of a plurality of antigen-specific IgEs.

In the present invention, "a substance that recognizes canine IgE and also recognizes the IgE of a laboratory animal other than dog" refers to a substance having the property of being capable of cross-recognizing canine IgE and the IgE of a laboratory animal other than dog. "A substance that recognizes human IgE and also recognizes the IgE of a laboratory animal" refers to a substance having the property of being capable of cross-recognizing human IgE and the IgE of a laboratory animal. Such substances include an antibody that recognizes both canine IgE and the IgE of a laboratory animal other than dog (hereinafter, sometimes abbreviated as "anti-canine IgE antibody"), an antibody that recognizes both human IgE and the IgE of a laboratory animal (hereinafter, sometimes abbreviated as "anti-human IgE antibody"), a high-affinity IgE receptor α subunit having an IgE-binding site (FcεRIα), nucleic acids (e.g., aptamers) and the like; however, ones whose specificity for IgE is high, and which has the property of equally recognizing canine (human) IgE and the IgE of a laboratory animal are desirable, so that the aforementioned anti-canine IgE antibody and antihuman IgE antibody are preferred. Such substances are useful as diagnostic reagents in the present invention.

The aforementioned antibody is preferably IgG. The antibody includes polyclonal antibodies and monoclonal antibodies, as well as chimeric antibodies, single-chain antibodies, and portions of these IgG antibodies possessing antigen bindability such as Fab fragments and fragments produced with a Fab expression library.

The anti-canine (-human) IgE antibody used in the methods of the present invention is not subject to morphological limitations, as far as it cross-recognizes canine (human) IgE and the IgE from at least 1 kind of laboratory animal, and does not recognize other immunoglobulins; the antibody may be a polyclonal antibody or monoclonal antibody to an immune antigen IgE. However, for highly accurate IgE quantitation, irrespective of the kind of antigen, a monoclonal antibody having a homogenous, stable binding site for each antigen-specific IgE is preferred. Furthermore, the antibody may be a chimeric antibody, single-chain antibody, or Fab fragment prepared on the basis of a gene that encodes the monoclonal antibody or a fragment produced using a Fab expression library.

The anti-canine (-human) IgE antibody used in the methods of the present invention is preferably prepared with a non-mouse animal, i.e., a rat, guinea pig, hamster or rabbit, when a mouse is chosen as a cross-recognizing laboratory animal. Likewise, the aforementioned antibody is preferably prepared with a non-rat animal, i.e., a mouse, guinea pig, hamster or rabbit, when a rat is chosen as a cross-recognizing laboratory animal.

The aforementioned anti-IgE monoclonal antibody can, for example, be obtained as described below when a mouse is chosen as a cross-recognizing laboratory animal. First, the spleen is extirpated from a rat immunized with purified total canine (human) IgE, and splenocytes are isolated. The isolated splenocytes and myeloma cells are cell-fused to prepare hybridoma cells, and a plurality of clones that recognize canine (human) IgE are screened using the culture supernatant of the hybridomas. Next, the screened hybridomas are again screened to determine whether they cross-recognize mouse IgE, and a hybridoma clone that produces an antibody that cross-recognizes canine (human) and rat IgEs is selected. Finally, the hybridoma is proliferated in the rat peritoneum, and ascites fluid is collected and purified by chromatography and the like.

The IgE used as an immunogen in preparing an antibody can be obtained by collecting blood or the like of high IgE titer, and purifying it by chromatography. The IgE can also be obtained by the operation of synthesizing an oligopeptide on the basis of gene sequence information supplied by GenBank and the like, or of cloning a DNA, constructing each plasmid, transfecting the DNA to a host, culturing the transformant, and recovering the protein from the culture. These operations can be performed by a method known to those skilled in the art, or a method described in the literature (Molecular Cloning, T. Maniatis et al., CSH Laboratory (1983), DNA Cloning, DM. Glover, IRL PRESS (1985)) and the like.

The aforementioned FcεRIα can be obtained according to, for example, the method described in Vet ImmunolImmunopathol. 78, 349-55 (2001). The aforementioned aptamer can be obtained according to, for example, methods described in previous reports (for example, Ellington et al., (1990) Nature, 346, 818-822; Tuerk et al., (1990) Science, 249, 505-510).

In the present invention, "an allergic disease" refers to a disease caused by IgE exceeding a certain level; examples include pollenosis, allergic rhinitis, allergic conjunctivitis, bronchial asthma, atopic dermatitis, contact dermatitis, post-vaccination allergy, anaphylaxis, food allergies, a disease causing hyper-IgE-emia, a disease estimated to involve IgE in the pathology thereof, and the like. Traditionally, whether or not the subject suffers an allergic disease has been determined with a positive intradermal reaction after intradermal inoculation of an antigen as an index, in the present application, the same can be confirmed by a positive or negative intradermal reaction.

The method of the present invention for quantifying an antigen-specific canine IgE comprises the following steps (A), (B), (C) and (D). The method of the present invention for quantifying antigen-specific human IgE comprises the same steps as those of the method of quantifying antigen-specific canine IgE, except that "a human biological sample" is used in place of "a biological sample from a subject dog" and "a substance that recognizes human IgE and also recognizes the IgE of a laboratory animal" is used in place of "a substance that recognizes canine IgE and also recognizes the IgE of a laboratory animal other than dog". Hereinafter, individual steps will be described with reference to dog cases, but those skilled in the art are able to understand that antigen-specific human IgE can likewise be quantified with the provision of the use of "a human biological sample" as the biological sample and "a substance that recognizes human IgE and also recognizes the IgE of a laboratory animal".

(A) Step for Contacting a Biological Sample from a Subject Dog with an Antigen to Bind the IgE in the Sample and the Antigen In the step (A), contact of the IgE in the above-described biological sample and an antigen may be performed while both are dissolved in a solvent, or while the antigen is immobilized on a solid phase. In the former case, a long time is taken for the binding of the IgE and the antigen to be completed while the IgE is allowed to react with the entire surface of the antigen. Thus, it is preferable that the biological sample and the antigen be contacted while the antigen is immobilized on a solid phase.

Immobilization of the antigen on a solid phase can be achieved by binding the antigen to the surface of a solid phase in common use in the technical art, such as a measuring container, by a method known per se. This binding to the solid phase can be achieved usually by dissolving the antigen in an appropriate buffer solution such as a citrate buffer solution, and contacting the surface of the solid phase with the antigen solution for an appropriate time (1 to 2 days). Examples of solid phase carriers suitable for antigen immobilization on a solid phase include microplate wells, plastic beads, magnetic beads, chromatography carriers (e.g., Sepharose™) and the like. After completion of immobilization on the solid phase, and after the antigen liquid is discarded, the solid phase carrier can be stored under refrigeration or at normal temperature in a dried state.

Furthermore, to suppress nonspecific adsorption and non-specific reactions, it is a common practice to bring a phosphate-buffered solution of fish gelatin, bovine serum albumin (BSA) or cow's milk protein and the like into contact with the solid phase to block the surface portion of the solid phase that has not become coated with the antigen with the fish gelatin, BSA or cow's milk protein and the like.

The biological sample from the subject dog may be brought into contact with the antigen in the state of a sample isolated from the living organism as it is, or may be brought into contact with the antigen after being diluted with a solvent such as water as appropriate. This contact is normally performed in a reaction vessel suitable for the means of measurement. When blood, serum, or blood plasma is used as a biological sample, it is preferable that the sample be used after being diluted to minimize the influence of interfering components other than IgE (IgG and the like). Degree of dilution can be set as appropriate according to the assay sensitivity for the conjugate of the IgE and the antigen. When blood, serum, or blood plasma is used as a biological sample in the ELISA method, the amount collected is normally sufficient at 0.5 to 2 ml, and these amounts allow a quantitation of 40 to 50 antigens.

Binding of the biological sample from the subject dog and the antigen is completed normally by keeping the sample to stand at 0 to 40° C., preferably at 4 to 30° C., for 0.5 minutes to 24 hours, preferably for 1 minute to 1 hour. During the binding step, stirring operation may be carried out as appropriate.

After completion of binding of the biological sample from the subject dog and the antigen, substances derived from the biological sample, other than the antigen-specific IgE, can be removed from the reaction system by washing the entire reaction system with an appropriate buffer solution and the like.

(B) Step for Measuring the IgE in a Standard Sample from a Laboratory Animal Other than Dog, Sensitized with the Antigen of the Step (a), Using a Substance that Recognizes Canine IgE and Also Recognizes the IgE of the Laboratory Animal, and Generating a Standard Curve The step (B) is a step for generating a standard curve that serves as a calibaration curve for quantifying antigen-specific canine IgE. This step may be performed concurrently with, or separately from, the step (A). If performed separately, this step may take place before or after the step (A), and may take place after completion of the step (A) and the step (C).

As a rule, the step (B) is performed for each antigen, and is repeated the same times as the number of antigens; however, this step may be completed in a single procedure, provided that the antigens involved possess crossreactivity with each other and can share a standard curve. Combinations of antigens possessing cross-reactivity include combinations of animal species or plant species belonging to the same taxonomic phylum/division or class or order; examples include beef and mutton, beef and pork, Japanese cedar pollen and Japanese cypress pollen, mite/tick and shrimp, latex and fruit and the like.

Specifically, measuring methods used in the step (B) and the step (C) described below include immunoassays, for example, enzyme-linked immunosorbent assay (ELISA method), immunochromatography, radioimmunoassay (RIA method), fluorescent immunoassay (FIA method), luminescence immunoassay, evanescent wave analysis method and the like. In particular, the ELISA method is suitable from the viewpoint of the ease of operation.

In one embodiment, the measurement of IgE in the step (B) is performed by applying the ELISA method. The standard sample from a laboratory animal for generating a standard curve is a biological sample from a laboratory animal sensitized with an antigen to have an elevated IgE antibody titer. Sensitization of the laboratory animal is performed by a conventional method. The standard sample is preferably a serum or blood plasma. A sample prepared by diluting the standard sample with a buffer solution or the like is brought into contact with an antigen immobilized to a solid phase to form a conjugate of the antigen and antigen-specific IgE. The binding of the standard sample and the antigen is performed in the same manner as the step (A), and is normally completed by keeping the sample to stand at 0 to 40° C., preferably at 4 to 30° C., for 0.5 minutes to 24 hours, preferably for 1 minute to 1 hour. During the binding reaction, stirring operation may be carried out as appropriate.

Next, as a primary antibody labeled with an enzyme, fluorescent dye or the like, the above-described anti-canine IgE antibody is used. Since the anti-canine IgE antibody cross-recognizes IgE from a laboratory animal, the antibody is reacted with the conjugate of the IgE from the laboratory animal and the antigen, and the conjugate is detected. If the primary antibody is not labeled with an enzyme, fluorescent dye or the like, a labeled antibody labeled with an enzyme or fluorescent dye (an antibody that binds to anti-canine IgE antibody) is used as a secondary antibody for its detection and bound to the primary antibody. Next, the entire reaction system is washed, and the enzyme and a substrate thereof are reacted. Binding of the primary antibody and the conjugate and binding of the primary antibody and the secondary antibody are normally completed by keeping them to stand at 0 to 40° C., preferably at 4 to 30° C., for 0.5 minutes to 2 hours, preferably for 1 minute to 2 hours. During the binding reaction, stirring operation may be carried out as appropriate.

The measurement of IgE in the step (B) involving the use of the ELISA method is performed by detecting a fluorescent signal or color development signal according to the combination of an enzyme and a substrate using a spectrophotometer or a (micro)plate reader and the like. A biological sample from a control laboratory animal not sensitized with any antigen is assayed in the same way, and the value obtained is subtracted as a background from the aforementioned signal.

Examples of the enzyme for labeling the aforementioned antibody include, if it is intended to produce a fluorescent substance by an enzyme reaction, β-D-galactosidase, β-D-glucuronidase and β-D-glucosidase. If it is intended to produce a color developing substance, peroxidase, alkaline phosphatase and glucose oxidase are included. Examples of the substrate agent used when β-D-galactosidase, β-D-glucuronidase or β-D-glucosidase is chosen as the enzyme include 4-methylumbelliferone (4-MU), 7-amide-4-methylcoumarine or 4-trifluoro-methylumbelliferone (4-TMU), respectively. When peroxidase is chosen as the enzyme, tetramethylbenzidine (TMB), o-phenylenediamine (OPD) and the like are used; when alkaline phosphatase is chosen, diaminobenzidine, o-nitrophenol, p-nitrophenol, p-nitrophenyl phosphate (PNPP), p-nitroaniline (PNA), 5-bromo-4-chloro-3-indolyl, 6-chloro-3-indolyl, 5-bromo-6-chloro-3-indoxyl-magenta, 6-chloro-3-indoxyl, N-methylindoxylyl and the like are used. Regarding the reaction quenching liquid and substrate solvent, conventionally known ones can be used without limitations according to the enzyme chosen as appropriate. The reaction conditions for the enzyme and the substrate can be set as appropriate for the combination chosen.

The standard curve is drawn by plotting measured values and expressing them by an approximation expression, with the concentration of the aforementioned standard sample in serial dilutions indicated by the axis of abscissa (the axis of ordinates), and the signal of antigen-bound IgE in the standard sample indicated in an arbitrary unit by the axis of ordinates (the axis of abscissa). The standard curve can be shown approximately as a straight line by logarithmically expressing the obtained values on the two axes.

Meanwhile, the concentration of total IgE in the sample from the laboratory animal, used as a standard sample, is measured separately. Assay kits for total IgE of laboratory animals such as mice are commercially available; concentrations of IgE corresponding to the signals of the same dilution series are determined using such a commercial product. Because the majority of antigen-specific IgE concentrations in an antigen-sensitized laboratory animal are equal to total IgE concentrations, it is possible to generate a standard curve for quantifying antigen-specific IgE by determining such a standard curve and the concentration of total IgE.

If the amount of antigen-specific IgE and the amount of total IgE in the serum from the antigen-sensitized laboratory animal are not equal, a standard curve (1) for the antigen-specific IgE is generated, after which the concentration of antigen-specific IgE can be determined as described below. A standard curve (2) is separately generated with the same assay system using a mouse monoclonal IgE against an available particular antigen (for example, mouse monoclonal IgE against Japanese cedar pollen antigen Cry j 1, mouse monoclonal IgE against ovalbumin), and a detection limit value is calculated in advance. Provided that the detection limit value on the standard curve (2) is 10 pg/ml, while taking the point where the signal of the standard curve (1) becomes zero or minus as the detection limit, the antigen-specific IgE concentration at the detection limit on the standard curve (1) can be deemed 10 pg/ml. Thus, a standard curve of the specific IgE for each antigen is prepared.

Even when mouse monoclonal IgE is not used, if the standard curve (1) and the standard curve for measuring the amount of total IgE are parallel when linearized, the point where the signal of the standard curve (1) becomes zero or minus is assumed to indicate one IgE molecule, and the amount of total IgE at that point is assumed to be the amount of antigen-non-specific IgE, and the number of molecules thereof is calculated (for example, in this case, the number of molecules of antigen-nonspecific IgE is assumed to be 1000). This makes it possible to calculate the relative ratio of the antigen-specific IgE and antigen-nonspecific IgE contained in the sensitized serum (for example, 1:1000), allowing the amount of antigen-specific IgE in the sensitized serum to be estimated from the amount of total IgE. If the standard curve (1) and the standard curve for measuring the amount of total IgE are not parallel when linearized, the amount of antigen-specific IgE can be estimated from the amount of total IgE in the same way by using the rate obtained by multiplying the foregoing relative ratio by the proportion of the gradients of the two straight lines.

(C) Step for Detecting the Conjugate Formed in the Step (A), Using the Substance that Recognizes Canine IgE and Also Recognizes the IgE of a Laboratory Animal Other Than Dog, Used in the Step (B)

In an embodiment, detection of the conjugate in the step (C) is performed by applying ELISA. As a primary antibody, the above-described anti-canine IgE antibody is used. As a secondary antibody for detecting the conjugate formed in the step (A), a labeled antibody labeled with an enzyme (an antibody that binds to the anti-canine IgE antibody) is used and bound to the primary antibody. Next, the entire reaction system is washed, and the enzyme and a substrate thereof are reacted. Subsequently, in the same manner as the step (B), a fluorescent signal or color development signal corresponding to the amount of the conjugate formed in the step (A) is detected using a spectrophotometer or a (micro)plate reader and the like.

In measuring the amount of IgE, to eliminate the influence of signals due to nonspecific binding and the like by the substances in the assay system, it is desirable that a control reference standard be prepared using a biological sample from a non-sensitized dog, and the background value be measured and subtracted from the measured value for the subject dog.

(D) Step for Quantifying the Amount of IgE in the Biological Sample from the Subject Dog Using the Amount of Conjugate Detected in the Step (C) and the Standard Curve Generated in the Step (B)

In the ELISA method, the amount of conjugate detected in the step (C) is detected as a signal of fluorescence unit or absorbance; by applying the obtained signal to the standard curve generated in the step (B), the concentration of antigen-specific IgE in the subject dog can be determined. The concentration of antigen-specific IgE in the biological sample from the subject dog can be quantified by multiplying the concentration determined on the standard curve by the dilution rate.

Because the method of quantification of the present invention allows the concentration of antigen-specific IgE to be expressed as an absolute amount, the concentration does not fluctuate largely among different testing organizations and different days of measurement, so that the method is suitable for monitoring antigen-specific IgE. Therefore, the essential nature of allergy can be traced fundamentally. Also, the method of quantification of the present invention enables a quantitative comparison of IgE between dogs and humans pivoted on the laboratory animals used to prepare the anti-canine (-human) IgE antibody that is an antigen-specific IgE detection reagent (mouse, rat, guinea pig, hamster, rabbit and the like), and is also helpful as an assay method for drug discovery research.

Other preferred embodiments of quantitation of antigen-specific canine IgE include a method involving the use of a substance that recognizes the above-described canine IgE as immobilized on a solid phase and also recognizes the IgE of a laboratory animal other than dog and an antigen labeled with a marker substance.

In the method of quantification of the present invention, the steps (A), (B), (C) and (D) may be performed for each antigen concurrently or separately. In the method of quantification of the present invention, the step (B) may be performed concurrently with, or separately from, the steps (A), (C) and (D). Hence, the step (B) is a step for generating a standard curve, which may be generated for each target antigen, and one standard curve common to a plurality of antigens may be generated and applied to the step (D).

The allergic disease diagnostic method of the present invention can be performed by a method comprising the following steps (A), (B), (C), (D) and (E):

(A) a step for contacting a biological sample from a subject dog with an antigen to bind the IgE in the sample and the antigen, (B) a step for measuring the IgE in a standard sample from a laboratory animal other than dog, sensitized with the antigen of the step (A), using a substance that recognizes canine IgE and also recognizes the IgE of the laboratory animal, and generating a standard curve, (C) a step for detecting the conjugate formed in the step (A), using the substance that recognizes canine IgE and also recognizes the IgE of a laboratory animal other than dog, used in the step (B), (D) a step for quantifying the amount of IgE in the biological sample from the subject dog using the amount of conjugate detected in the step (C) and the standard curve generated in the step (B), and (E) a step for determining the presence or absence or severity of an allergic disease on the basis of the results of the quantitation in the step (D).

The steps (A) to (D) in the diagnostic method of the present invention are the same as the steps (A) to (D) in the above-described method of quantitation. The diagnostic method of the present invention comprises the step (E) in addition to the steps (A) to (D).

When a dog (e.g., beagle dog) is experimentally sensitized with an antigen, the antigen-specific IgE concentration at which the intradermal reaction to the antigen becomes positive can serve as a value for determining the presence or absence of a disease (in this case, meaning "the presence or absence of onset"). Any value under the aforementioned concentration can be defined as "indicating a potential for contracting an allergic disease" (that is, the dog can be judged to have been sensitized by the antigen, but to be in a stage where accumulation of IgE is necessary to cause onset, and is likely to contract an allergy in the future, because the IgE against the antigen is detected at a low value).

Meanwhile, in cases where IgE is detected but there are no symptoms, the dog can be judged to suffer "atopy". Assuming the concept of "determining the presence or absence of an allergic disease" to be "determine the presence or absence of atopy", detection of IgE at a certain value that enables the detection thereof is sufficient.

In a reasonable number of cases, the amount of antigen-specific IgE is measured by the steps (A) to (D) of the diagnostic method of the present invention, and an intradermal reaction to the antigen is tested, whereby a level of the amount of antigen-specific IgE that causes a positive intradermal reaction can be determined empirically.

Therefore, in the diagnostic method for allergic disease of the present invention, in the step (E), the presence or absence of an allergic disease can be determined by calculating a measured value of IgE exceeding the aforementioned level, and the severity of an allergic disease can be determined by comparing the magnitudes of measured values of IgE.

If an amount of antigen-specific IgE exceeding the detection limit is detected by the diagnostic method of the present invention, the subject dog, irrespective of the presence or absence of symptoms, can be diagnosed as suffering an atopic disease caused by the antigen.

In the diagnostic method for allergic disease of the present invention, the steps (A) to (D) are performed for a plurality of kinds of antigens, and on the basis of the concentrations of antigen-specific IgEs obtained, an allergic disease against which antigen is serious can be determined comprehensively. On the basis of the results of the determination, an appropriate measure for the treatment of a the serious allergic disease, such as drug therapy or immunotherapy and the like, can be taken.

The diagnostic method for allergic disease of the present invention can be applied not only to the diagnosis of allergic diseases, but also to the tracing of the therapeutic effects for allergic diseases, rating of healing or remission, tools for avoiding allergens (tick-proof futon, air purifiers, air hole filters, cleaners, allergen-removing sprays and the like), efficacy determination and tracing necessary for the development of anti-allergic drugs and the like.

The methods of the present invention for quantifying antigen-specific canine IgE and for diagnosing a canine allergic disease can be performed as they are as a method of quantifying antigen-specific human IgE and a diagnostic method for a human allergic disease by using a biological sample from a human subject and a substance that recognize human IgE and also recognizes the IgE of a laboratory animal, in place of a biological sample from a subject dog and a substance that recognize canine IgE and also recognizes the IgE of a laboratory animal other than dog.

In another aspect, the present invention provides a kit for quantifying antigen-specific canine IgE. The quantitation kit comprises a substance that recognizes canine IgE and also recognizes the IgE of a laboratory animal other than dog, an antigen, and a standard sample from the laboratory animal sensitized with the antigen, contained in separate containers. The quantitation kit of the present invention may contain a biological sample from the aforementioned laboratory animal not sensitized with the aforementioned antigen as a control sample in still another container. Because the quantitation kit can be marketed in packages, it is useful as a reagent for conveniently carrying out the method of quantification of the present invention. How to use the quantitation kit is as described above herein.

In still another aspect, the present invention provides a diagnostic kit for a canine allergic disease. The diagnostic kit comprises a substance that recognizes canine IgE and also recognizes the IgE of a laboratory animal other than dog, an antigen, a standard sample from the laboratory animal sensitized with the antigen, and a control sample from the laboratory animal not suffering any allergic disease, in separate containers. The diagnostic kit of the present invention may contain a control sample from a dog not suffering any allergic disease in still another container. The diagnostic kit of the present invention can be marketed as a diagnostic reagent in a package, and is useful as a reagent for conveniently carrying out the diagnostic method of the present invention. How to use the diagnostic kit is as described above herein.

The kit of the present invention can be provided as a quantitation kit for antigen-specific human IgE and diagnostic kit for human allergic disease by containing a substance that recognizes human IgE and also recognizes the IgE of a laboratory animal, in place of a substance that recognizes canine IgE and also recognizes the IgE of a laboratory animal other than dog.

EXAMPLES

The present invention is hereinafter described in more detail by means of the following Examples, by which, however, the present invention is never limited.

Example 1

Screening for Monoclonal Antibody that Exhibits Cross Reactivity to Canine Antibody and Mouse IgE As antibodies for quantifying canine IgE, rat ascites fluids containing an anti-canine IgE monoclonal antibody (clone 1-2 ascites fluid, clone 1-10 ascites fluid and clone 1-13 ascites fluid) were purchased from Nippon Zenyaku Kogyo Co., Ltd.

Mouse IgE (Bethyl Laboratories, Inc., USA) was immobilized on a 96-well microtiter plate at 20 ng/well at 4° C. overnight. Next, a dilution of each of the aforementioned 3 kinds of clone ascites fluids was placed in the microtiter plate and incubated at 4° C. for 1 hour and washed, after which a peroxidase-labeled goat anti-rat IgE antibody (Bethyl Laboratories, Inc., USA) was added, a color was developed according to a conventional method, and the absorbance thereof was measured (FIG. 1). As the clone 1-2 ascites fluid was diluted, the absorbance decreased. The clone 1-10 ascites fluid and clone 1-13 ascites fluid did not recognize mouse IgE (control ascites fluids).

Figure 2:
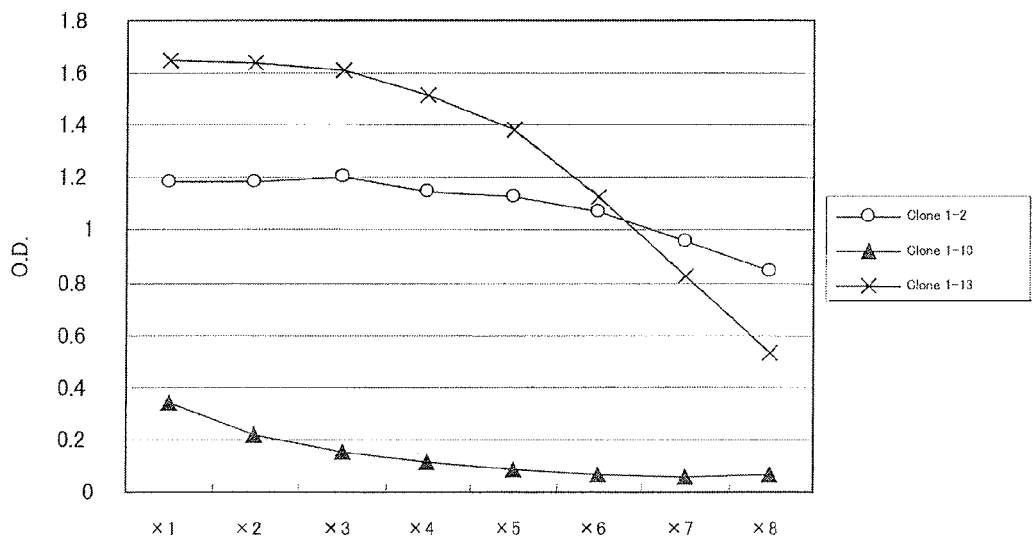
FIG. 2 A graph confirming that rat anti-canine IgE antibodies (clones) recognize canine IgE using the ELISA method. The axis of ordinates and the axis of abscissa indicate absorbance and dilution rate of antibody preparation, respectively.

Canine IgE (Bethyl Laboratories, Inc., USA) was assayed in the same manner as with the aforementioned mouse IgE (FIG. 2). As the clone 1-2 ascites fluid and clone 1-13 ascites fluid were diluted, the absorbances decreased. The clone 1-13 ascites fluid did not recognize canine IgE.

From the results shown above, it was found that a rat IgG JO that recognizes both mouse IgE and canine IgE is present in the clone 1-2 ascites fluid.

Example 2

Purification of Anti-Mouse×Canine IgE Antibody

Figure 3:
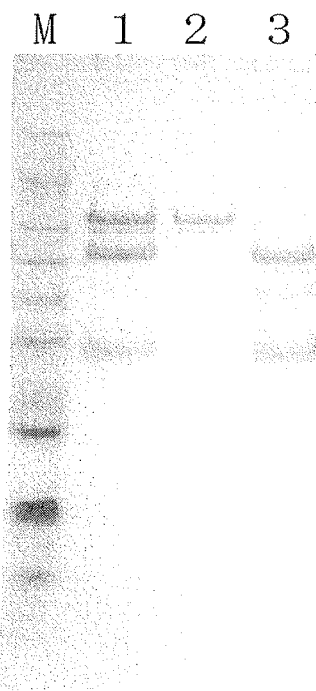
FIG. 3 An electrophoretic photograph of an antibody that cross-recognizes mouse and canine IgEs during and after purification. M, marker. 1, flow-through liquid after DEAE cellulose chromatography and cation exchange chromatography. 2, flow-through liquid after Protein G column chromatography (the desired antibody adsorbed using Protein G and removed). 3, liquid obtained by eluting the desired antibody from Protein G column (purified rat IgG antibody).

Next, using the three stages of DEAE cellulose chromatography, cation exchange chromatography, and Protein G column chromatography, rat IgG was purified from clone 1-2 ascites fluid liquid, which had been confirmed as being cross-reactive with canine and mouse IgEs (FIG. 3). The purified rat IgG was labeled with biotin using NHS-PEO4-Biotin (PIERCE Company). Subsequently, unreacted biotin was removed by gel filtration using the Sephadex G25 column (NAP-5 Columns, GE Healthcare Bioscience Company). Biotinylated rat IgG (biotinylated anti-mouse×canine IgE antibody) was used in the following Examples.

Example 3

Quantitation of Japanese Cedar Pollen-Specific IgE

Japanese cedar pollen crude antigen (400 μg) and aluminum hydroxide (20 mg) were subcutaneously administered to each beagle dog (female, 5-month old) twice at a 2-week interval to prepare a Japanese cedar pollen-sensitized dog. Canine serum with elevated Japanese cedar pollen-IgE was collected from this dog, and this was used as the subject sample.

Meanwhile, mice sensitized with Cry j 1 (major antigen of Japanese cedar pollen) were prepared for use to generate a standard curve. Cry j 1 (5 μg) and aluminum hydroxide (2 mg) were administered to each mouse (BALB/c, female, 8-week old) at a 1-week interval. Serum was collected from this mouse, and the Cry j 1-IgE concentration in the serum was separately quantified. To quantify mouse Cry j 1-IgE, the ELISA method for measuring antigen-specific mouse IgE was used with a standard curve generated using mouse Cry j 1-IgE (commercially available from Medicine & Biological Laboratories Co., Ltd.).

A Cry j 1 antigen liquid (3 μg/ml) was added to a 96-well flat-based microplate for ELISA assay at 100 μL/well, and the plate was kept to stand at 4° C. overnight to immobilize the antigen on the solid phase. Subsequently, after blocking with 1% fish gelatin PBS, the plate was washed, and the Cry j 1-sensitized mouse serum having a Cry j 1 (major antigen of Japanese cedar pollen)-specific IgE concentration of 6958 ng/ml was serially diluted and added. Meanwhile, an 8100-fold dilution of Cry j 1-sensitized canine serum was concurrently prepared and used in measurements.

With the addition of biotinylated anti-mouse×canine IgE antibody (0.25 μg/ml), the plate was incubated at room temperature for 2 hours, after which the plate was washed, streptavidin-conjugated beta galactosidase was added, and the plate was further incubated at room temperature for 1 hour, after which a beta galactosidase substrate (4-Methylumbelliferyl (3-D-galactopyranoside) was added; after the plate was kept to stand at room temperature for 30 minutes, the fluorescence intensity for each well was measured using a fluorescence plate reader (Spectra Max Gamini XPS, Molecular Devices).

Figure 4:
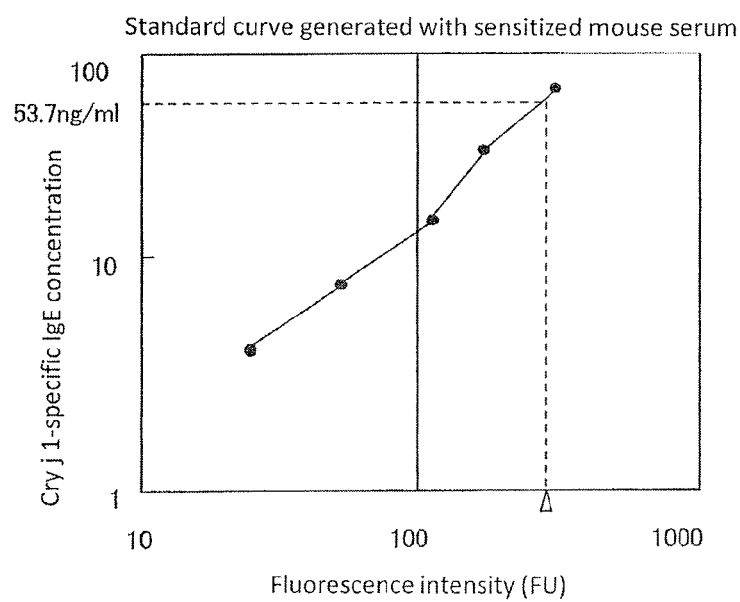
FIG. 4 Shown is a measurement of Japanese cedar pollen-specific IgE concentrations in Japanese cedar pollen-sensitized canine serum using a standard curve generated using Cry j 1-sensitized mouse serum. The standard curve was generated using the Cry j 1-sensitized mouse serum, based on which the absolute amount of Japanese cedar pollen-specific IgE in a serum of a dog sensitized with Japanese cedar pollen was measured. The axis of ordinates and the axis of abscissa indicate Cry j 1-specific IgE concentration and fluorescence intensity, respectively.
Figure 5:
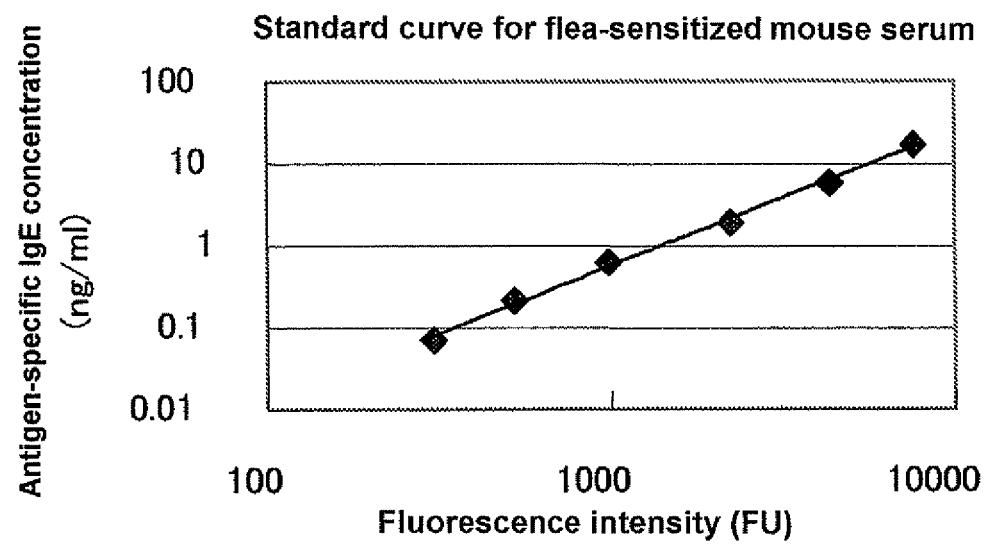
FIG. 5 Shown is a measurement of flea antigen-specific IgE concentrations in case dog serum using a standard curve generated using flea-sensitized mouse serum. The axis of ordinates and the axis of abscissa indicate antigen-specific IgE concentration and fluorescence intensity as obtained by the ELISA method, respectively.
Figure 6:
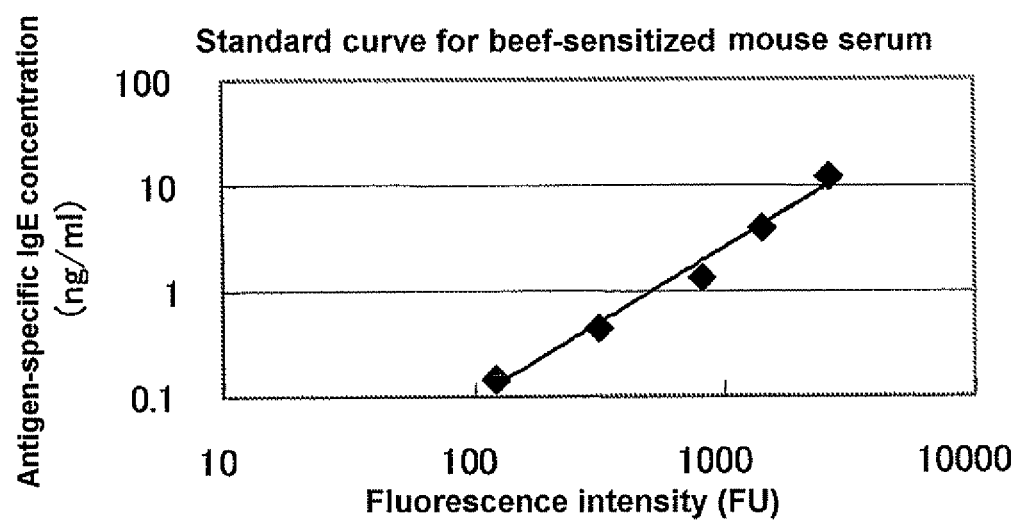
FIG. 6 Shown is a measurement of beef antigen-specific IgE concentrations in case dog serum using a standard curve generated using beef-sensitized mouse serum. The axis of ordinates and the axis of abscissa indicate antigen-specific IgE concentration and fluorescence intensity as obtained by the ELISA method, respectively.
Figure 7:
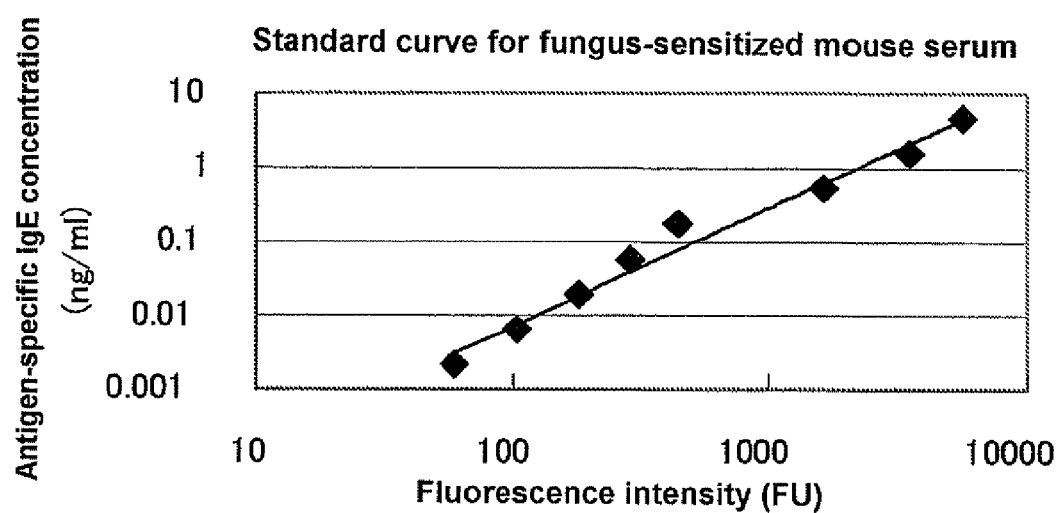
FIG. 7 Shown is a measurement of *Aspergillus* antigen-specific IgE concentrations in case dog serum using a standard curve generated using *Aspergillus*-sensitized mouse serum. The axis of ordinates and the axis of abscissa indicate antigen-specific IgE concentration and fluorescence intensity as obtained by the ELISA method, respectively.

As a result, a standard curve could be generated using the Cry j 1-sensitized mouse serum (FIG. 4). Because the concurrently measured fluorescence intensity of a dilution of a serum from a Japanese cedar pollen-sensitized dog on this standard curve was 2417 FU, the concentration of Cry j 1-specific IgE contained in this diluted serum was found to be 53.7 ng/ml (FIG. 4, arrowhead); the amount of Cry j 1-specific IgE in this serum was calculated from the dilution rate (8100 times) to be 434700 ng/ml.

Example 4

The amounts of flea-, beef-, and *Aspergillus* (fungus, *Aspergillus Nidulans*)-specific IgEs in the sera from four open-field case dogs diagnosed with typical canine atopic dermatitis (see below) were measured.

Case 1: Chihuahua, male at 9 years of age
Case 2: Yorkshire Terrier, contracepted female at 7 years of age
Case 3: Shiba, male at 5 years of age
Case 4: Shiba, castrated male at 7 years of age The standard curve used was generated using pool sera from four mice sensitized with respective antigen liquids. For antigen sensitization of mice, 4 mice per antigen were used. Each antigen liquid, purchased from Greer Company (USA), was intraperitoneally injected to Balb/c mice (female, 8 to 10 weeks of age) at 50 μg of antigen/mouse along with 2 mg/mouse of alum. Two shots were given every week; serum was collected at 3 to 4 weeks after the start of sensitization.

The pool sera from the mice sensitized with the respective antigens were analyzed using the Mouse IgE ELISA Quantitation Kit (Bethyl Laboratories, Inc., USA) to determine the amounts of total IgE. The IgE concentrations in the various pool sera are shown below.

Flea-sensitized serum 17171.9 ng/ml
Beef-sensitized serum 5937.7 ng/ml
*Aspergillus*-sensitized serum 4666.2 ng/ml Serum from a normal dog (beagle dog) was concurrently assayed, the fluorescence intensity was subtracted from the actual measured value of fluorescence intensity for each case dog serum, and this was used as the fluorescence intensity for the case dog.

As a result, the amounts of various antigen-specific IgEs in the case dogs had the values shown below.

TABLE 1

| | Flea antigen-specific IgE | | Beef antigen-specific IgE | | *Aspergillus* antigen-specific IgE | |
| --- | --- | --- | --- | --- | --- | --- |
| | Fluorescence intensity | ng/ml | Fluorescence intensity | ng/ml | Fluorescence intensity | ng/ml |
| Case 1 | 509 | 197.2 | ND | ND | 166 | 17.6 |
| Case 2 | ND | ND | ND | ND | 1387 | 521.3 |
| Case 3 | ND | ND | ND | ND | 289 | 42.5 |
| Case 4 | 2008 | 1884.0 | 2936 | 7967.3 | ND | ND |

(When the actual measured value of fluorescence intensity for a case dog was lower than the fluorescence intensity for the normal dog serum, the finding was described as "not detected (ND)".

From the results shown above, the major cause of the allergic disease in each case dog can be determined. It can be estimated that the major cause was a flea antigen for case 1, an *Aspergillus* antigen for cases 2 and 3, and a beef antigen for case 4.

If a sensitized serum is prepared using small animals such as mice, the purchasing price per animal is within 2000 yen and the duration of rearing is about 2 months, the cost for serum preparation per antigen is within 5000 yen. Therefore, it is possible to construct an assay system for 50 antigens at a cost of around 200000 yen (a cost about one-fortieth of the cost for dogs). The amount of serum required for each measurement is 1 to 2 µL; the amount of serum collectable from each mouse allows approximately 1000 to 2000 runs of testing (equivalent to daily measurements for about 3 years).

INDUSTRIAL APPLICABILITY

According to the present invention, absolute amounts of antigen-specific canine or human IgE can be known accurately, making it possible to quantitatively trace the seasonality of allergies and quantitatively monitor therapeutic effects. Because the absolute amounts of IgEs specific for different antigens can be compared, it is possible to comprehensively determine which antigen is the cause of the allergic disease being currently problematic in each diseased dog or patient. Based thereon, it is possible to provide useful information for the treatment of allergic diseases.

This application is based on a patent application No. 2008-125292 filed in Japan (filing date: May 12, 2008), the contents of which are incorporated in full herein.

The invention claimed is:

1. A method of quantifying an antigen-specific canine IgE, comprising the following steps (A) to (D):
   (A) a step for contacting a biological sample from a subject dog with an antigen to bind IgE in the biological sample, whereby a complex of the IgE and the antigen is formed,
   (B) a step for measuring IgE in a standard sample of a mouse or rat, sensitized with the antigen of the step (A), by contacting the standard sample with the antigen to bind the IgE in the standard sample and with a rat or mouse monoclonal antibody, respectively, that recognizes canine IgE and also recognizes the mouse or rat IgE with equal affinity, wherein the monoclonal antibody does not recognize immunoglobulins other than IgE, to detect the bound standard IgE, and generating a standard curve,
   (C) a step for detecting an amount of the complex formed in the step (A) by contacting the complex with the same monoclonal antibody used in the step (B), and
   (D) a step for quantifying an amount of antigen-specific canine IgE in the biological sample from the subject dog by comparing the amount of complex detected in the step (C) and the standard curve generated in the step (B).

2. The method according to claim 1, wherein the steps (A), (B), (C) and (D) are performed for each antigen concurrently or separately, or wherein the step (B) is performed concurrently with, or separately from, the steps (A), (C) and (D).

3. The method according to claim 1, wherein the biological sample from the subject dog is blood, serum, blood plasma, nasal discharge, tear, saliva, urine or feces.

4. The method according to claim 1, wherein the monoclonal antibody is a rat monoclonal antibody that recognizes canine IgE and mouse IgE with equal affinity.

5. A quantitation kit for antigen-specific canine IgE in a subject dog comprising (a) a rat or mouse monoclonal antibody that recognizes canine IgE and mouse or rat IgE, respectively, with equal affinity, wherein the antibody does not recognize immunoglobulins other than IgE, (b) an antigen, and (c) a standard sample from mouse or rat sensitized with the antigen, contained in separate containers.

6. The kit according to claim 5, further comprising a control sample from a dog, mouse, or rat not suffering any allergic disease, contained in a separate container, thereby enabling the subject dog to be diagnosed with a canine allergic disease.

7. The kit according to claim 6, wherein the allergic disease is at least 1 kind selected from the group consisting of pollenosis, allergic rhinitis, allergic conjunctivitis, bronchial asthma, atopic dermatitis, contact dermatitis, post-vaccination allergy, anaphylaxis, food allergy, a disease causing hyper-IgE-emia and a disease estimated to involve IgE in the pathology thereof.

* * * * *